United States Patent [19]

Rosenberger et al.

[11] 4,197,236
[45] Apr. 8, 1980

[54] PIPERIDINE STABILIZERS

[75] Inventors: Siegfried Rosenberger, Riehen; Samuel Evans, Basel, both of Switzerland

[73] Assignee: Ciba-Geigy Corporation, Ardsley, N.Y.

[21] Appl. No.: 931,439

[22] Filed: Aug. 7, 1978

Related U.S. Application Data

[63] Continuation of Ser. No. 788,711, Apr. 19, 1977, abandoned.

[30] Foreign Application Priority Data

Apr. 28, 1976 [CH] Switzerland .................. 5333/76

[51] Int. Cl.$^2$ .................. C08K 5/34; C07D 211/46
[52] U.S. Cl. .................. 260/45.8 N; 546/222; 546/224
[58] Field of Search .................. 260/45.8 N, 293.64, 260/293.73, 293.76, 293.81, 293.82, 293.77; 546/222, 224

[56] References Cited

U.S. PATENT DOCUMENTS

| | | | |
|---|---|---|---|
| 3,414,538 | 12/1968 | Prinz et al. | 260/45.85 B |
| 3,422,059 | 1/1969 | Taylor et al. | 260/45.85 B |
| 3,640,928 | 2/1972 | Murayama et al. | 260/45.8 N |
| 3,684,765 | 8/1972 | Matsui et al. | 260/45.8 N |
| 3,992,390 | 11/1976 | Holt et al. | 260/45.8 N |
| 3,993,655 | 11/1976 | Rasberger et al. | 260/45.8 N |
| 4,021,432 | 5/1977 | Holt et al. | 260/293.64 |

Primary Examiner—V. P. Hoke
Attorney, Agent, or Firm—Wenderoth, Lind & Ponack

[57] ABSTRACT

Compounds of the general formula I

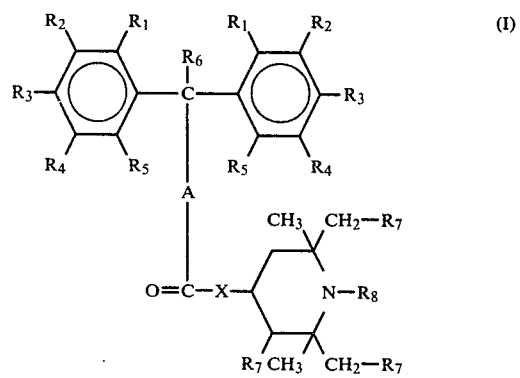

or their acid addition salts in which one of $R_1$ and $R_3$ is —OH and the other is hydrogen and $R_2$ denotes $C_1$–$C_{12}$-alkyl, $C_5$–$C_7$-cycloalkyl, $C_6$–$C_{10}$-aryl or $C_7$–$C_9$-aralkyl and $R_4$ and $R_5$ are hydrogen, $C_1$–$C_{12}$-alkyl, $C_5$–$C_7$-cycloalkyl, $C_6$–$C_{10}$-aryl or $C_7$–$C_9$-aralkyl and $R_6$ denotes hydrogen, $C_1$–$C_{12}$-alkyl, $C_5$–$C_7$-cycloalkyl, phenyl or benzyl and $R_7$ is hydrogen or $C_1$–$C_8$-alkyl and $R_8$ is hydrogen, oxyl, $C_1$–$C_{12}$-alkyl, $C_3$–$C_6$-alkenyl, $C_3$–$C_4$-alkinyl, $C_2$–$C_{21}$-alkoxyalkyl, $C_7$–$C_8$-aralkyl, 2,3-epoxypropyl, an aliphatic acyl group with 1-4 C atoms or one of the groups —CH$_2$COOR$_9$, —CH$_2$—CH(R$_{10}$)—OR$_{11}$, —COOR$_{12}$ or —CONHR$_{12}$, in which R$_9$ is $C_1$–$C_{12}$-alkyl, $C_3$–$C_6$-alkenyl, phenyl, $C_7$–$C_8$-aralkyl or cyclohexyl and R$_{10}$ is hydrogen, methyl or phenyl and R$_{11}$ denotes hydrogen or an aliphatic or aromatic, araliphatic or alicyclic acyl group with 1-18 C atoms, in which the aromatic part can optionally be substituted by chlorine, $C_1$–$C_4$-alkyl or $C_1$–$C_8$-alkoxy and/or by hydroxyl, or a group

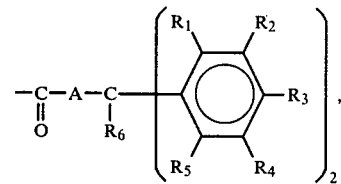

and R$_{12}$ denotes $C_1$–$C_{12}$-alkyl, cyclohexyl, phenyl or benzyl and X is —O— or —NR$_{13}$—, in which R$_{13}$ denotes hydrogen, $C_1$–$C_{12}$-alkyl, $C_5$–$C_7$-cycloalkyl or $C_7$–$C_9$-aralkyl and A is one of the groups —($C_nH_{2n}$)—, which can optionally be interrupted by —S— or

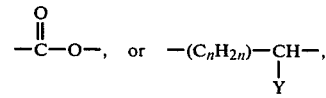

in which n denotes 0 to 12 and Y is one of the groups

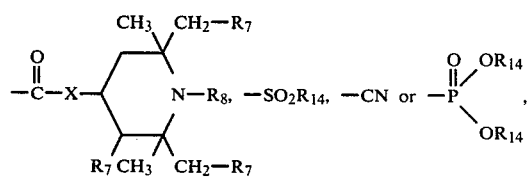

in which R$_7$, R$_8$ and X have the meaning defined above and R$_{14}$ denotes $C_1$–$C_{12}$-alkyl, phenyl or tolyl as stabilizers for organic material.

5 Claims, No Drawings

PIPERIDINE STABILIZERS

This is a continuation of application Ser. No. 788,711, filed Apr. 19, 1977, now abandoned.

The present invention relates to new piperidine derivatives of alkylidene bisphenols, their manufacture and their use for stabilising organic material and also to the organic material stabilised with the aid of these derivatives.

It is known to employ derivatives of sterically hindered phenols as stabilisers for organic polymers to protect them against thermo-oxidative degradation and against light ageing. Many of these phenol derivatives have the disadvantage that they discolour the organic polymer in a troublesome manner, either already during incorporation or when exposed to the action of light or on contact with industrial off-gases or also on contact with hot water and this greatly restricts the extent to which they can be used industrially. An example of a known and commercially available derivative is n-octadecyl β-(3,5-di-tert.-butyl-4-hydroxyphenyl)-propionate, compare British patent specification No. 990,304. In the U.S. Pat. No. 3,455,875 there have been described similar bisphenols differing from one another in the ester moiety, which however in combined light and heat protection are inferior to the compounds according to the invention. New compounds have now been found which, surprisingly, are not only outstandingly suitable for stabilising organic materials, especially organic polymers, but, when used in this way, remain colourless even under the said conditions and protect the organic material against discolouration for a long period. This means that the new compounds stabilise the organic material both against degradation and against discolouration.

The invention relates to new compounds of the general formula I

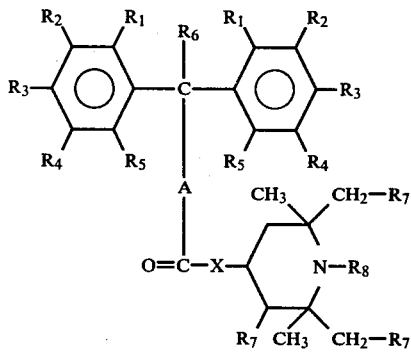

or acid addition salts thereof, in which one of $R_1$ and $R_3$ is —OH and the other is hydrogen and $R_2$ denotes $C_1$–$C_{12}$-alkyl, $C_5$–$C_7$-cycloalkyl, $C_6$–$C_{10}$-aryl or $C_7$–$C_9$-aralkyl and $R_4$ and $R_5$ are hydrogen, $C_1$–$C_{12}$-alkyl, $C_5$–$C_7$-cycloalkyl, $C_6$–$C_{10}$-aryl or $C_7$–$C_9$-aralkyl and $R_6$ denotes hydrogen, $C_1$–$C_{12}$-alkyl, $C_5$–$C_7$-cycloalkyl, phenyl or benzyl and $R_7$ is hydrogen or $C_1$–$C_8$-alkyl and $R_8$ is hydrogen, oxyl, $C_1$–$C_{12}$-alkyl, $C_3$–$C_6$-alkenyl, $C_3$–$C_4$-alkinyl, $C_2$–$C_{21}$-alkoxyalkyl, $C_7$–$C_8$-aralkyl, 2,3-epoxypropyl, an aliphatic acyl group with 1–4 C atoms or one of the groups —$CH_2COOR_9$, —$CH_2$—$CH(R_{10})$—$OR_{11}$, —$COOR_{12}$ or —$CONHR_{12}$, in which $R_9$ is $C_1$–$C_{12}$-alkyl, $C_3$–$C_6$-alkenyl, phenyl, $C_7$–$C_8$-aralkyl or cyclohexyl and $R_{10}$ is hydrogen, methyl or phenyl aralphatic or aromatic, aralphatic or alicyclic acyl group with 1–18 C atoms, in which the aromatic part can optionally be substituted by chlorine, $C_1$–$C_4$-alkyl or $C_1$–$C_8$-alkoxy and/or by hydroxyl, or a group

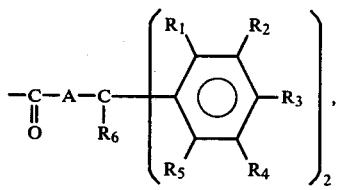

and $R_{12}$ denotes $C_1$–$C_{12}$-alkyl, cyclohexyl, phenyl or benzyl and X is —O— or —$NR_{13}$—, in which $R_{13}$ denotes hydrogen, $C_1$–$C_{12}$-alkyl, $C_5$–$C_7$-cycloalkyl or $C_7$–$C_9$-aralkyl and A is one of the groups —$(C_nH_{2n})$—, which can optionally be interrupted by —S— or

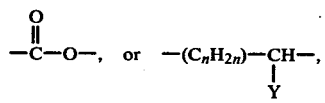

in which n denotes 0 to 12 and Y is one of the groups

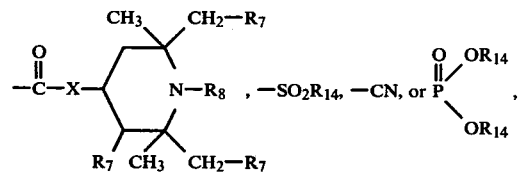

in which $R_7$, $R_8$ and X have the meaning defined above and $R_{14}$ denotes $C_1$–$C_{12}$-alkyl, phenyl or tolyl.

As branched or unbranched $C_1$–$C_{12}$-alkyl, $R_2$, $R_4$ and $R_5$ can be, for example, methyl, ethyl, isopropyl, sec.-butyl, tert.-butyl, amyl, n-hexyl, 1,1,3,3-tetramethylbutyl, tert.-nonyl, n-decyl or n-dodecyl. Alkyl groups with 1–6 C atoms, and especially those with 1–4 C atoms, are preferred as $R_2$ and $R_4$. Alkyl groups with 1–6 C atoms, and especially those with 1–4 C atoms, are preferred as $R_5$ and particularly preferentially $R_5$ denotes methyl.

As $C_5$–$C_7$-cycloalkyl, $R_2$, $R_4$ and $R_5$ are, for example, cyclopentyl, methylcyclopentyl, cyclohexyl or methylcyclohexyl.

As $C_6$–$C_{10}$-aryl, $R_2$, $R_4$ and $R_5$ are, for example, phenyl, α-naphthyl or β-naphthyl, especially phenyl.

As $C_7$–$C_9$-aralkyl, $R_2$, $R_4$ and $R_5$ are, for example, benzyl, α-phenylethyl or 2-phenyl-propyl, especially benzyl.

An branched or unbranched $C_1$–$C_{12}$-alkyl, $R_6$ can be, for example, methyl, ethyl, isopropyl, tert.-butyl, amyl, n-hexyl, tert.-octyl, iso-nonyl, n-decyl or n-dodecyl. Alkyl groups with 1–6 C atoms are preferred and methyl is very particularly preferred.

As $C_1$–$C_8$-alkyl, $R_7$ is, for example, methyl, ethyl, iso-propyl, n-butyl, amyl, n-hexyl or n-octyl. Alkyl groups with 1–4 C atoms, and especially ethyl and methyl, are preferred. Compounds in which $R_7$ denotes methyl are to be singled out in particular.

As $C_1$–$C_{12}$-alkyl, $R_8$ is, for example, methyl, ethyl, n-propyl, n-butyl, n-pentyl, n-hexyl, n-octyl, n-decyl or n-dodecyl. Alkyl groups with 1–8 C atoms, especially those with 1–4 C atoms, and above all methyl, are preferred.

As $C_3$–$C_6$-alkenyl, $R_8$ is, for example, allyl, 2-butenyl or 2-hexenyl, especially allyl.

As $C_3$–$C_4$-alkinyl, $R_8$ is, for example, propargyl.

If $R_8$ denotes $C_2$–$C_{21}$-alkoxyalkyl, the alkyl part can contain 1–3 C atoms and the alkoxy part can consist of 1–18 C atoms, as in, for example, methoxymethyl, ethoxymethyl, 2-methoxyethyl, 2-ethoxyethyl, 2-n-butoxyethyl, 3-n-butoxyethyl, 2-octoxyethyl or 2-octadecyloxyethyl. Compounds in which $R_8$ denotes an alkoxyalkyl group with 2–6 C atoms are to be mentioned in particular.

As $C_7$–$C_8$-aralkyl, $R_8$ is, for example, benzyl or α-phenylethyl.

As an aliphatic acyl group with 1–4 C atoms, $R_8$ is, for example, formyl, acetyl, acryloyl or crotonyl, especially acetyl.

If $R_8$ is the group —$CH_2COOR_9$, $R_9$, as $C_1$–$C_{12}$-alkyl, denotes, for example, methyl, ethyl, isopropyl, n-butyl, isobutyl, t-butyl, isopentyl, n-octyl, n-decyl or n-dodecyl. $R_9$ is preferably $C_1$–$C_4$-alkyl. As $C_3$–$C_6$-alkenyl, $R_9$ is, for example, allyl, 2-butenyl or 2-hexenyl. As $C_7$–$C_8$-aralkyl, $R_9$ is, for example, benzyl or α-phenylethyl.

If $R_8$ is the group —$CH_2$—$CH(R_{10})$—$OR_{11}$, $R_{10}$ denotes hydrogen, methyl or phenyl, especially hydrogen. As an aliphatic, aromatic, alicyclic or araliphatic $C_1$–$C_{18}$-acyl radical which is optionally substituted in the aromatic part by chlorine or $C_1$–$C_4$-alkyl, such as methyl, ethyl, n-propyl, or t-butyl, or by $C_1$–$C_8$-alkoxy, such as methoxy, ethoxy, butoxy or octoxy, and/or by hydroxyl, $R_{11}$ is, for example, acetyl, propionyl, butyryl, octanoyl, dodecanoyl, stearoyl, acryloyl, benzoyl, chlorobenzoyl, toluoyl, isopropylbenzoyl, 2,4-dichlorobenzoyl, 4-methoxybenzoyl, 3-butoxybenzoyl, 2-hydroxybenzoyl, 3,5-di-t-butyl-4-hydroxybenzoyl, β-(3,5-di-t-butyl-4-hydroxyphenyl)-propionyl, phenylacetyl, cinnamoyl or hexahydrobenzoyl.

If $R_8$ is the group —$COOR_{12}$, $R_{12}$, as $C_1$–$C_{12}$-alkyl, is, for example, methyl, ethyl, isobutyl, n-hexyl, n-octyl, n-decyl or n-dodecyl. Alkyl groups with 1–4 C atoms are preferred as $R_{12}$.

X denotes —O— or —$NR_{13}$—, especially —O—. If X is —$NR_{13}$—, $R_{13}$ can preferably be hydrogen, or, as $C_1$–$C_{12}$-alkyl, can denote methyl, ethyl, isopropyl, isobutyl, n-pentyl, n-hexyl, tert.-nonyl, n-decyl or n-dodecyl. As alkyl, $R_{13}$ is particularly preferentially methyl.

A can preferably be —$(C_nH_{2n})$—, which can optionally be interrupted by —S— or

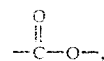

with the keto group being nearer to the bisphenolic molecule moiety, or can also denote the group

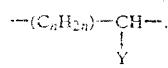

It can be methylene, dimethylene, trimethylene, tetramethylene, hexamethylene, octamethylene, decamethylene, 2-thiabutylene, 2-thiahexamethylene, 3-thiaoctamethylene, 3-thiadodecamethylene,

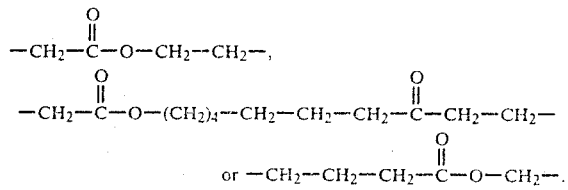

n is a number from 0 to 12. n is preferably 0 to 6 and especially 0 to 3. Particularly preferentially, n is 0 to 2.

If Y denotes the radical —$SO_2R_{14}$, $R_{14}$, as $C_1$–$C_{12}$-alkyl, is methyl, ethyl, n-butyl, n-hexyl, n-octyl, n-decyl or n-dodecyl.

Salts of compounds which are to be mentioned in particular are acid addition salts with inorganic or organic acids. The salts can be obtained in the customary manner and the free bases, which, in turn, are preferred, can be obtained again from the salts. Suitable acids for forming a salt are, in particular, inorganic acids, such as hydrochloric acid, sulphuric acid and phosphoric acid, but also organic acids, such as, for example, p-toluenesulphonic acid.

Compounds of the formula I in which $R_1$ is hydrogen and $R_2$ denotes $C_1$–$C_{12}$-alkyl and $R_3$ is —OH and $R_4$ is hydrogen or $C_1$–$C_{12}$-alkyl and $R_5$ denotes hydrogen or $C_1$–$C_6$-alkyl and $R_6$ is hydrogen or $C_1$–$C_{12}$-alkyl and $R_7$ is hydrogen or $C_1$–$C_4$-alkyl and $R_8$ is hydrogen, $C_1$–$C_8$-alkyl, $C_3$–$C_4$-alkenyl or alkinyl, $C_2$–$C_6$-alkoxyalkyl, $C_7$–$C_8$-aralkyl, acetyl, acryloyl or crotonoyl or one of the groups —$CH_2$—$COOR_9$, —$CH_2$—$CH(R_{10})$—$OR_{11}$, —$COOR_{12}$ or —$CONHR_{12}$, in which $R_9$ is $C_1$–$C_4$-alkyl, $C_3$–$C_4$-alkenyl, phenyl, $C_7$–$C_8$-aralkyl or cyclohexyl and $R_{10}$ is hydrogen, methyl or phenyl and $R_{11}$ denotes hydrogen or an aliphatic, aromatic, alicyclic or araliphatic acyl group with 1–18 C atoms, in which the aromatic part can optionally be substituted by chlorine, $C_1$–$C_4$-alkyl, $C_1$–$C_8$-alkoxy and/or hydroxyl, and $R_{12}$ is $C_1$–$C_{12}$-alkyl and X is —O— or —$NR_{13}$—, in which $R_{13}$ denotes hydrogen or $C_1$–$C_{12}$-alkyl, and A is one of the groups —$(C_nH_{2n})$— or

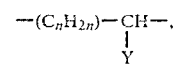

in which n is 0 to 6 and Y is one of the groups

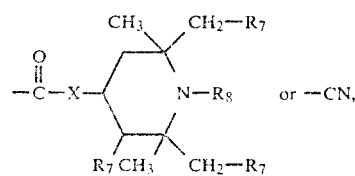

in which X, $R_7$ and $R_8$ have the meaning defined above, are preferred.

Compounds of the formula I in which $R_1$ denotes hydrogen and $R_2$ denotes $C_1$–$C_6$-alkyl and $R_3$ is —OH and $R_4$ denotes hydrogen or $C_1$–$C_6$-alkyl and $R_5$ is hydrogen or $C_1$–$C_4$-alkyl and $R_6$ is hydrogen or $C_1$–$C_6$-alkyl and $R_7$ denotes hydrogen, methyl or ethyl and $R_8$ is hydrogen, $C_1$–$C_4$-alkyl, allyl, propargyl, $C_2$–$C_6$-alkoxyalkyl, acetyl, acryloyl or crotonoyl or one of the groups —$CH_2$—$COOR_9$, —$CH_2$—$CH(R_{10})$—$OR_{11}$ —$COOR_{12}$ or —$CONHR_{12}$, in which $R_9$ is $C_1$–$C_4$-alkyl and $R_{10}$ denotes hydrogen or methyl and $R_{11}$ denotes hydrogen and $R_{12}$ is $C_1$–$C_4$-alkyl and X is —O— or —$NR_{13}$—, in which $R_{13}$ is hydrogen or methyl, and A denotes one of the groups —$(C_nH_{2n})$— or

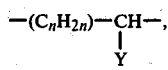

in which n is 0 to 2 and Y is one of the groups

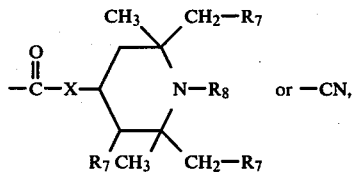

in which X, $R_7$ and $R_8$ have the meaning defined above, are particularly preferred.

Compounds of the formula I in which $R_1$ is hydrogen and $R_2$ is $C_1$–$C_4$-alkyl and $R_3$ is —OH and $R_4$ is hydrogen or $C_1$–$C_4$-alkyl and $R_5$ denotes hydrogen or methyl and $R_6$ is hydrogen or methyl and $R_7$ is hydrogen or methyl and $R_8$ denotes hydrogen, methyl, allyl, propargyl or acetyl and X is —O— or —$NR_{13}$—, in which $R_{13}$ is hydrogen or methyl, and A is one of the groups —$(C_nH_{2n})$— or

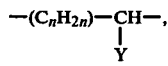

in which n is 0 to 2 and Y denotes the group

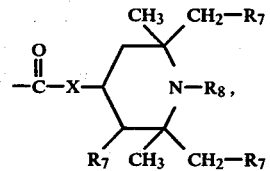

in which X, $R_7$ and $R_8$ have the meaning defined above, are particularly important.

Amongst these, compounds of the formula I in which $R_1$ is hydrogen and $R_2$ is $C_1$–$C_4$-alkyl and $R_3$ denotes —OH and $R_4$ denotes hydrogen and $R_5$ denotes hydrogen or methyl and $R_6$ is hydrogen or methyl and $R_7$ is hydrogen and $R_8$ is hydrogen, methyl or acetyl and X is —O— or —$NR_{13}$—, in which $R_{13}$ denotes hydrogen, and A is one of the groups —$(C_nH_{2n})$— or

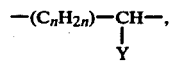

in which n is 0 to 2 and Y denotes the group

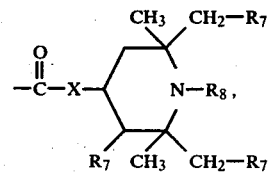

in which X, $R_7$ and $R_8$ have the meaning defined above, are to be mentioned above all.

Examples of compounds of the formula I are: 2,2,6,6-tetramethyl-N-acetyl-piperidin-4-yl di-(3-t.-butyl-6-methyl-4-hydroxy-phenyl)-acetate, 2,2,6,6-tetramethyl-piperidin-4-yl 4,4-di-(3-t.-butyl-5-methyl-2-hydroxy-phenyl)-valerate, 3,3-di-(3-t.-butyl-4-hydroxy-phenyl)-butyric acid 2,3,6-trimethyl-2,6-diethyl-piperidin-4-yl-amide, di-(2,2,6,6-tetramethyl-N-methyl-piperidin-4-yl) 2-[3,3-di-(3-t.-butyl-6-methyl-4-hydroxy-phenyl)-propyl]-malonate, di-(3-t.-butyl-5-methyl-2-hydroxy-phenyl)-acetic acid 2,2,6,6-tetramethyl-piperidin-4-yl-amide, 2,3,6-trimethyl-2,6-diethyl-piperidin-4-yl di-(3-t.-butyl-4-hydroxy-phenyl)-acetate, 4,4-di-(3-t.-butyl-6-methyl-5-hydroxy-phenyl)-valeric acid 2,2,6,6-tetramethyl-piperidin-4-yl-amide and 2,2,6,6-tetramethyl-N-methyl-piperidin-4-yl 4,4-di-(3,5-di-t.-butyl-4-hydroxy-phenyl)-valerate.

The compounds of the formula I can be manufactured by various methods which are in themselves known.

Thus, for example, it is possible to react approximately one mol of a di-(alkylhydroxyphenyl)-alkane carboxylic acid, or an ester or the chloride thereof, of the formula II

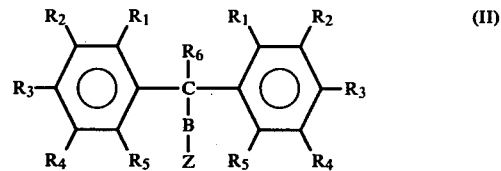

in which $R_1$, $R_2$, $R_3$, $R_4$, $R_5$ and $R_6$ have the same meaning as in formula I and Z denotes the radical —COOH, —COO—alkyl or —COCl and B is —$(C_nH_{2n})$— or

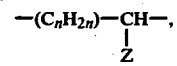

with a piperidine of the formula III

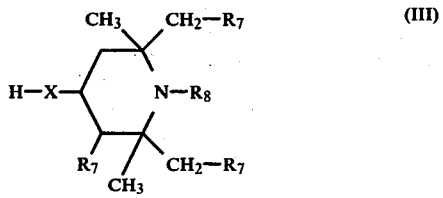

in which X, $R_7$ and $R_8$ have the same meaning as in formula I, by the customary transesterification or aminolysis processes. In these reactions it is advantageous to use a water-binding agent, such as, for example, (dicyclohexyl)-carbodiamide, or, alternatively, to remove the water by azeotropic distillation.

The manufacture of the compounds of the formula II is described in, for example, German Offenlegungsschrift No. 1,953,333 and is carried out by reacting approximately one mol of a compound of the formula IV

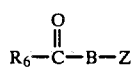

in which the symbols $R_6$, B and Z have the meaning described above, with approximately 2 mols of a phenol of the formula V

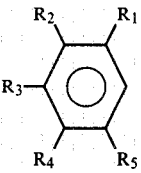

in which the symbols $R_1$, $R_2$, $R_3$, $R_4$ and $R_5$ have the same meaning as in formula I, in the presence of acid catalysts, such as HCl, $H_2SO_4$ or $BF_3$-etherate.

Another process variant for the manufacture of the compounds of the formula I concerns the reaction of approximately one mol of a compound of the formula VI

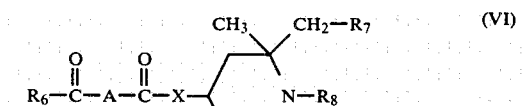

in which $R_6$, $R_7$, $R_8$, A and X have the same meaning as in formula I, with approximately 2 mols of a phenol of the formula V

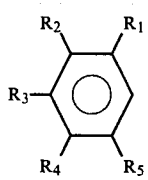

in which $R_1$, $R_2$, $R_3$, $R_4$ and $R_5$ have the meaning defined in formula I. This condensation reaction can be carried out under the reaction conditions described in German Offenlegungsschrift No. 1,953,333.

The compounds of the formula VI are manufactured by the customary transesterification or aminolysis processes, a 4-hydroxy- or 4-amino-piperidine of the formula III

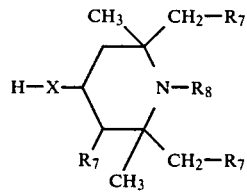

in which $R_7$, $R_8$ and X have the meaning defined above, being reacted with approximately one mol of a formyl- or keto-carboxylic acid, or of an ester or the acid chloride thereof, of the formula IV

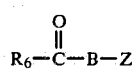

in which $R_6$, B and Z have the meaning defined above.

The starting materials of the formula IV and V are known or, if they are new, can be obtained according to processes which are in themselves known.

The compounds of the formula III are known, for example the 4-hydroxy-piperidines are known from German Offenlegungsschrift No. 2,352,658 and the 4-amino-piperidines are known from U.S. Pat. No. 3,684,765. The 4-OH compounds can, in general, be manufactured from the corresponding 4-oxopiperidines of the formula VII

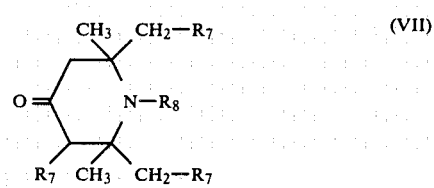

by reduction, for example by catalytic hydrogenation over Raney nickel, whilst the 4-$NH_2$ compounds are, for example, obtainable from VII by means of a reductive reaction with ammonia.

The 4-oxopiperidines of the formula VII, in which $R_8$ is hydrogen, can be manufactured by various processes.

Thus, for example, the reaction of an aliphatic ketone with ammonia is described by W. Traube in Chem. Ber. 41, 777 (1908).

4-Oxopiperidines of the formula VII in which $R_8$ denotes hydrogen can also be manufactured analogously to the process described in U.S. Pat. No. 3,513,170. In this process, an alkyl-substituted tetrahydropyrimidine is rearranged by hydrolysis in the presence of an acid catalyst.

N-H compounds of the formula VII which possess substituents of different types in the 2-position and the 6-position can be manufactured by reacting a ketone of the formula $CH_3$—CO—$CH_2$—$R_7$ with ammonia. The pyrimidine formed is hydrolysed, as described in Helv. Chim. Acta 30, 114 (1947), to give an amino-ketone of the formula VIII.

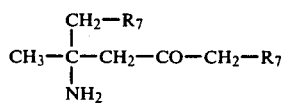

In a second process step, the compounds of the formula VIII are reacted with ammonia and a ketone $CH_3$—CO—$CH_2$—$R_7$, as is described, for example, in Monatsh. Chemie 88, 464 (1957). The compounds of the formula VII in which $R_8$ denotes hydrogen can be obtained from the pyrimidine, which thus results, by hydrolysis.

Compounds of the formula VII in which $R_8$ does not denote hydrogen can be manufactured from the corresponding N-H compounds by substitution. The reactions concerned are the substitution reactions customary for secondary amines, although these proceed more slowly due to the steric hindrance by the methyl group or the group —CH₂—R₇. The N-H compounds can be reacted, for example, with alkyl halides, alkenyl halides, aralkyl halides or alkoxyalkyl halides, with dialkyl sulphates, with epichlorohydrins or with esters of chlorocarboxylic acids, such as chloroacetates, or acid chlorides or acid anhydrides.

The group —CH₂—CH(R₁₀)—OR₁₁ can be introduced by reacting the N-H piperidines with an epoxide of the formula

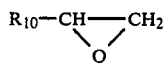

and subsequently acylating the reaction product with an acyl chloride of the formula R₁₁Cl.

Compounds of the 2,2,6,6-tetramethyl-4-(carbalkoxycyanomethyl)-piperidine type, which can be used as an intermediate product, are also known as intermediate products from British patent specification No. 1,214,426.

According to the present invention, the compounds of the formula I can be used as stabilisers for plastics in order to protect them against damage due to the action of oxygen, heat and light. Examples of such plastics are the polymers listed in German Offenlegungsschrift No. 2,456,864 on pages 12–14.

The stabilisation of polyolefins and styrene polymers and of polyurethanes is of particular importance and the compounds of the formula I are outstandingly suitable for this. Examples of such polymers are high density polyethylene and low density polyethylene, polypropylene, ethylene-propylene copolymers, polystyrene, styrene-butadiene-acrylonitrile copolymers, mixtures of polyolefines or of styrene polymers, and polyurethanes based on polyethers or polyesters, in the form of films, lacquers, elastomers or foams.

The stabilisers are added to the plastics in a concentration of 0.01 to 5% by weight, relative to the material to be stabilised. Preferably, 0.03 to 1.5, and particularly preferentially 0.2 to 0.6, % by weight of the compounds, calculated relative to the material to be stabilised, are incorporated into the latter.

The incorporation can be effected after the polymerisation, for example, by mixing the compounds, and optionally further additives, into the melt by the methods customary in the art, before or during shaping, or by applying the dissolved or dispersed compounds to the polymer, if appropriate with subsequent evaporation of the solvent.

The new compounds can also be added to the plastics to be stabilised in the form of a master batch which contains these compounds, for example in a concentration of 2.5 to 25% by weight.

In the case of crosslinked polyethylene, the compounds are added prior to crosslinking.

The invention therefore also relates to the plastics which are stabilised by the addition of 0.01 to 5% by weight of a compound of the formula I and which optionally can also contain other known and customary additives. The plastics stabilised in this way can be used in very diverse forms, for example as films, fibres, tapes or profiles, or as binders for lacquers, adhesives or putties.

Examples which may be mentioned of further additives, together with which the stabilisers which can be used according to the invention can be employed, are: antioxidants, such as simple 2,6-dialkylphenols, derivatives of alkylated hydroquinones, hydroxylated thiodiphenyl ethers, alkylidene-bisphenols, O-, N- and S-benzyl compounds, hydroxybenzylated malonates, hydroxybenzyl-aromatic compounds, s-triazine compounds, amides of β-(3,5-di-tert.-butyl-4-hydroxyphenyl)-propionic acid, esters of β-(3,5-di-tert.-butyl-4-hydroxy-phenyl)-propionic acid, esters of β-(5tert.-butyl-4-hydroxy-3-methylphenyl)-propionic acid, esters of 3,5-di-tert.-butyl-4-hydroxyphenylacetic acid, acylaminophenols, benzylphosphonates and aminoaryl derivatives, UV-absorbers and light protection agents, such as 2-(2'-hydroxyphenyl)-benztriazoles, 2,4-bis-(2'-hydroxyphenyl)-6-alkyl-s-triazines, 2-hydroxybenzophenones, 1,3-bis-(2'-hydroxybenzoyl)-benzenes, esters of optionally substituted benzoic acids and acrylates, and also nickel compounds, sterically hindered amines, oxalic acid diamides, metal deactivators, phosphites, compounds which destroy peroxide, polyamide stabilisers, basic Co stabilisers, PVC stabilisers, nucleating agents or other additives such as, for example, plasticisers, lubricants, emulsifiers, fillers, carbon black, asbestos, kaolin, talc, glass fibres, pigments, optical brighteners, flameproofing agents and antistatic agents.

Examples of further additives, together with which the stabilisers which can be used according to the invention can be employed, are given in German Offenlegungsschrift No. 2,427,853 on pages 18–24.

The manufacture and use of the compounds according to the invention is described in more detail in the examples which follow.

EXAMPLE 1

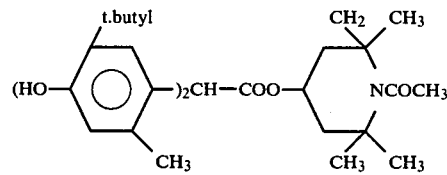

16.4 g of 2,2,6,6-tetramethyl-N-acetylpiperidin-4-yl diethoxyacetate are allowed to run slowly dropwise into a mixture of 16.4 g of 2-t-butyl-5-methylphenol and 30 ml of boron trifluoride-diethyl etherate, at 5° C., whilst stirring, and the batch is stirred for a further 20 hours at 5° C. and then carefully added to about 500 ml of ice water, whilst stirring, and the organic phase is taken up in ether. After repeated washing with water and drying with calcium chloride, the ether phase is evaporated in vacuo and the oily residue is ground with acetonitrile. 2,2,6,6-Tetramethyl-N-acetyl-piperidin-4-yl di-(3-t-butyl-6-methyl-4-hydroxy-phenyl)-acetate with a melting point of 270° C. then crystallises out. (Stabiliser no. 1).

The colourless crystals are isolated and dried.

EXAMPLE 2

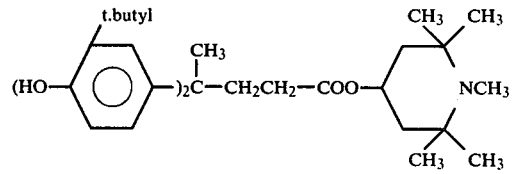

42.7 g of ethyl 4,4-di-(4-hydroxy-3-t-butyl-phenyl)-valerate and 17.1 g of 1,2,2,6,6-pentamethyl-4-hydroxypiperidine in 120 ml of mesitylene, with the addition of 100 mg of lithium amide as the catalyst, are heated to 160° C. in a nitrogen atmosphere for 5 hours, whilst stirring. During this time, the ethanol formed distils off in the stream of nitrogen and can be measured in a cold trap. After cooling, 100 ml of toluene are added to the batch and the solution is washed with water, dried with calcium chloride and evaporated in vacuo. The crystalline residue is recrystallised from acetonitrile or chlorobenzene. In this way 1,2,2,6,6-pentamethyl-piperidin-4-yl 4,4-di-(4-hydroxy-3-t-butyl-phenyl)-valerate (stabiliser no. 2) is obtained as a white crystalline powder with a melting point of 203° C.

EXAMPLE 3

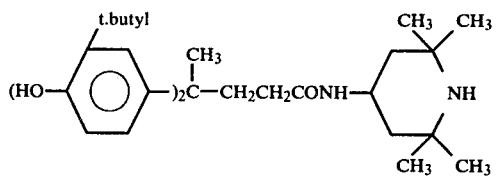

39.8 g of 4,4-di-(4-hydroxy-3-t-butylphenyl)-valeric acid, 15.6 g of 2,2,6,6-tetramethyl-4-amino-piperidine and 20.6 g of dicyclohexylcarbodiimide in 400 ml of toluene are heated to 70° C. for 3 hours, whilst stirring. A solution is formed and the dicyclohexylurea formed gradually partly crystallises out from this.

After cooling, the solution is washed several times with water, dried over calcium chloride and freed from by-products by column chromatography. 4,4-Di-(4-hydroxy-3-t-butyl-phenyl)-valeric acid (2,2,6,6-tetramethyl-piperidin-4-yl)-amide (stabiliser no. 3), which is thus obtained in a pure form, crystallises on grinding with hexane and then has a melting point of 133° C.

EXAMPLE 4

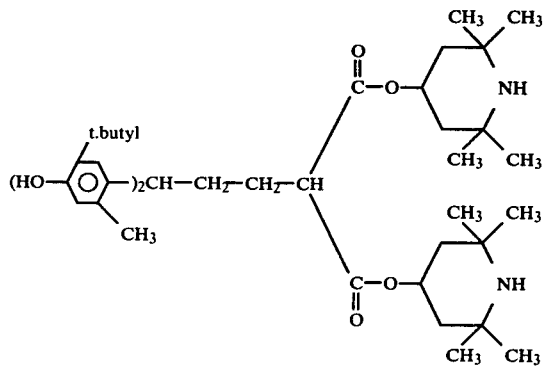

0.1 g of lithium amide is added, at a temperature of 110° C., to 10.3 g of diethyl 2-[3,3-di-(3-t.-butyl-6-methyl-4-hydroxyphenyl)-propyl]-malonate and 6.28 g of 2,2,6,6-tetramethyl-4-hydroxy-piperidine in 150 ml of xylene. The reaction mixture is stirred at this temperature for 15 hours, the ethanol formed is distilled off as an azeotrope with xylene and, after cooling, the solvent is distilled off in vacuo. This gives di-(2,2,6,6-tetramethyl-piperidin-4-yl) 2-[3,3-di-(3-t.-butyl-6-methyl-4-hydroxyphenyl)-propyl]-malonate as a pale yellow viscous oil (stabiliser no. 4).

EXAMPLE 5

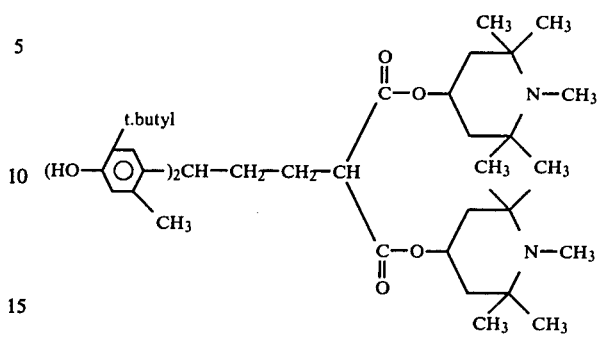

If the reaction described in example 4 is carried out with 10.5 g of diethyl 2-[3,3-di-(3-t.-butyl-6-methyl-4-hydroxy-phenyl)-propyl]-malonate and 6.8 g of 1,2,2,6,6-pentamethyl-4-hydroxy-piperidine, this gives, with an otherwise identical procedure, di-(1,2,2,6,6-pentamethyl-piperidin-4-yl) 2-[3,3-di(3-t.-butyl-6-methyl-4-hydroxy-phenyl)-propyl]-malonate as a crystalline compound with a melting point of 130°–135° C. (Stabiliser no. 5).

EXAMPLE 6

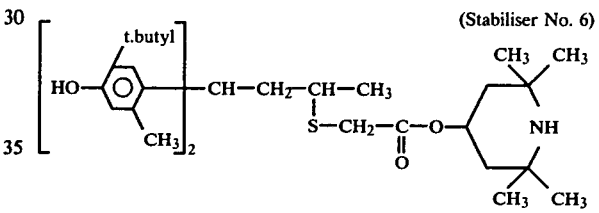

(Stabiliser No. 6)

Step I 70.1 g of crotonaldehyde are added dropwise at 25° C. in the course of 1 hour to 106.1 g of methyl thioglycolate containing 2 ml of triethylamine. The reaction mixture is heated for 3 hours at 50° C. and, after cooling, neutralised with 1.6 ml of acetic acid. Distillation of the clear yellow solution yields 108.4 g of the thioaldehyde of the formula

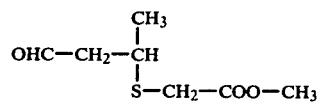

which boils at 93°–95° C./0.5 mm Hg.

Step II 41 g of boron trifluoride etherate are added dropwise at 0°–5° C. to a solution of 17.6 g of the thioaldehyde of Step I and 32.8 g of 2-tert.-butyl-5-methylphenol in 5.0 ml of methanol. The reaction solution is stirred at this temperature for 2 hours. After the temperature has reached 23° C., water is added after 16 hours and the product is extracted with ether. The solvent is removed by evaporation to leave 41 g of a yellow oil which crystallises out on standing. Recrystallisation from ligroin/toluene yields 20.3 g of the bisphenol of the formula

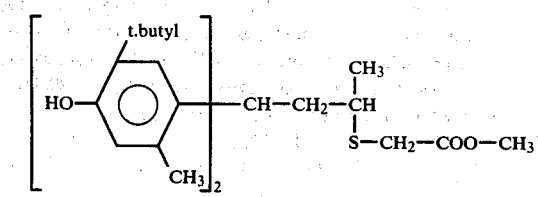

which has a melting point of 138°–139° C.

Step III

A solution of 5.0 g of the bisphenol of Step II and 1.57 g of 2,2,6,6-tetramethyl-4-hydroxypiperidine and 0.1 g of lithium-amide in 100 ml of toluene is heated for 16 hours at 110°–120° C. After cooling of the solution and removal of the solvent by filtration under suction, 5.7 g of a viscous oil can be obtained, which crystallises out on standing at room temperature. Recrystallisation from acetone yields 2.7 g of the white crystalline Stabiliser No. 6, which melts at 90° C.

EXAMPLE 7

(Stabiliser No. 7)

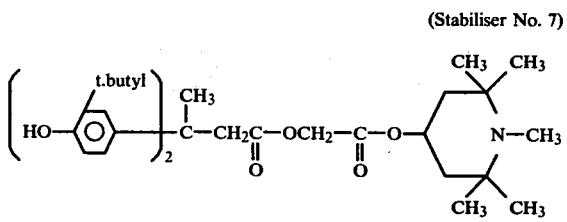

Step I 15.4 g of 3,3-di-(4-hydroxy-3-t-butylphenyl)-butyric acid are dissolved in a mixture of 150 ml of water, 40 ml of N sodium hydroxide solution and 150 ml of methanol; the solution is filtered and the filtrate is concentrated at 80° in vacuo completely to dryness, towards the end with the addition of toluene. To the crystalline residue of the sodium salt are then added 250 ml of anhydrous dioxane and 4.35 g of methyl chloroacetate and the mixture is heated at 100° C. for 4 hours. The pink solution is clarified and the solvent is removed in vacuo. The semi-solid residue yields on recrystallisation from toluene/hexane crystalline methyl 3,3-di-(4-hydroxy-3-t-butylphenyl)-butyral-hydroxyacetate, m.p. 141° C.

Step II 9.1 g of the methyl ester of Stage I and 3.4 g of 4-hydroxy-1,2,2,6,6-pentamethyl piperidine are suspended in 40 ml of mesitylene, the suspension is heated at 90° C. in a nitrogen atmosphere, with stirring, and 50 mg of lithium amide are added. The reaction mixture is then held at 150° for 15 hours, cooled, and taken up in 200 ml of toluene. After a brief washing with ice-water, the toluene phase is dried over calcium chloride, and the solvent is removed in vacuo. After prolonged standing, the residue solidifies in crystalline form. Recrystallisation from toluene/hexane yields (1,2,2,6,6-pentamethyl-piperidin-4-yl)3,3-di-(4-hydroxy-3-t-butylphenyl)-butyryl-hydroxyacetate, m.p. 112° C. (Stabiliser No. 7).

EXAMPLE 8

100 parts of polypropylene (melt index 2.6 g/10 min., 230° C./2160 g) are thoroughly mixed, in a shaking apparatus, for 10 minutes with 0.2 part in each case of an additive given in the following Table I. The mixture obtained is kneaded at 200° C. for 10 minutes in a Brabender plastograph; the resulting mixture is subsequently pressed in a platen press at 260° C. platen temperature to form 1 mm thick sheets, from which are stamped strips 1 cm in width and 17 cm in length.

The testing of the effectiveness of the additives contained in the test strips is carried out by heat ageing at 135° C. and 149° C., with a test strip containing no additive serving as a comparison. Three test strips from each formulation are used. The end point is defined as being that at which decomposition of the test strip, a condition easily recognisable by virtue of complete embrittlement, commences. The results are given in days.

Table I

| | Days until start of decomposition | |
|---|---|---|
| Stabiliser No. | at 135° C. | at 149° C. |
| without additive | 1 | — |
| 1 | 28 | 6 |
| 2 | 59 | 18 |
| 3 | 42 | 8 |
| 4 | 49 | 8 |
| 5 | 48 | 11 |
| 6 | 30 | 12 |
| 7 | 42 | 11 |

EXAMPLE 9

The test specimens described in Example 8 are furthermore tested for colour stability, (a) after incorporation (Table II, column 2),
(b) after 150 hours' exposure to light in a Xenotest apparatus of the firm Hanau (Table II, column 3),
(c) after treatment for 1 week with boiling water (Table II, column 4).

For the evaluation, an empirical colour scale is used in which 5 signifies colourlessness, 4 a slight discolouration just perceptible, and 3, 2, 1 and <1 denote a successively more intense discolouration.

Table II

| | Colour evaluation according to scale 1–5 | | |
|---|---|---|---|
| Stabiliser No. | after incorporation | after exposure to light | boiling water 1 week |
| without additive | 5 | 5 | 4–5 |
| 1 | 4 | 5 | 4–5 |
| 2 | 4–5 | 5 | 4–5 |
| 3 | 4–5 | 5 | 4–5 |
| 4 | 4–5 | 5 | 4–5 |
| 5 | 4 | 5 | 4 |
| 6 | 4–5 | 4–5 | 4–5 |
| 7 | 4–5 | 5 | 4–5 |

EXAMPLE 10

100 parts of polypropylene (melt index 2.6 g/10 min., 230° C./2160 g are thoroughly mixed in a shaking apparatus for 10 minutes with 0.1 part in each case of an additive given in the following Table III and 0.3 part of dilaurylthiodipropionate, with the procedure otherwise being as in Example 8. As a comparison there is used a test strip containing only 0.3 part of dilaurylthiodipropionate.

Table III

| Stabiliser No. | Days until start of decomposition | |
|---|---|---|
| | 135° C. | 149° C. |
| comparison | 11 | 5 |
| 1 | 53 | 18 |
| 2 | 61 | 21 |
| 3 | 65 | 24 |
| 4 | 51 | 24 |
| 5 | 69 | 28 |
| 6 | 44 | 16 |
| 7 | 61 | 18 |

EXAMPLE 11

The test specimens described in Example 10 are furthermore tested for colour stability (a) after incorporation (Table IV, column 2), (b) after 200 hours exposure to light in a Xenotest apparatus of the firm Hanau (Table IV, column 3), (c) after treatment for 1 week with boiling water (Table IV, column 4).

For Table IV there is used an empirical colour scale in which 5 denotes colourlessness, 4 a slight discolouration just perceptible, and 3, 2, 1 and <1 signify successively more intense discolouration.

Table IV

| Stabiliser No. | Colour evaluation according to scale 1-5 | | |
|---|---|---|---|
| | after incorporation | after exposure to light | boiling water 1 week |
| 1 | 4-5 | 5 | 4-5 |
| 2 | 4-5 | 5 | 5 |
| 3 | 5 | 5 | 5 |
| 4 | 5 | 5 | 4-5 |
| 5 | 4-5 | 5 | 4-5 |
| 6 | 5 | 4-5 | 4-5 |
| 7 | 5 | 5 | 5 |

EXAMPLE 12

Light-stability Testing in Polypropylene 100 parts of polypropylene powder (Moplen, fibre grade, Montedison) are homogenised with 0.2 part of a stabiliser given in the following Table V for 10 minutes at 200° C. in a Brabender plastograph. The mixture thus obtained is removed as quickly as possible from the kneader and pressed in a toggle lever press to form 2–3 mm thick sheets. A part of the obtained sheet material is cut out and pressed between two highly polished sheets in a hand-hydraulic laboratory press for 6 minutes at 260° C. under a pressure of 12 tons to obtain a 0.5 mm thick sheet, which is immediately quenched in cold water. Under exactly identical conditions there is produced from this 0.5 mm thick sheet the 0.1 mm thick test sheet. From this are then stamped sections each 60×44 mm and these are exposed to light in the Xenotest 150.

At regular intervals of time, these specimens are removed from the exposure apparatus and tested in an IR spectrophotometer for their carbonyl content. The increase of the carbonyl extinction at $5.85\mu$ on exposure is a measure for the photooxidative degradation of the polymer (see L. Balaban et al., J. Polymer Sci. Part C, 22, 1059–1071 (1969); J. F. Heacock, J. Polymer Sci. Part A-1, 22, 2921–34 (1969); D. J. Carlsson and D. M. Wiles, Macromolecules 2, 587–606 (1969)) and from experience is associated with a deterioration of the mechanical properties of the polymer.

The protective action of the stabilisers according to the invention can be seen from Table V:

Table V

| Stabiliser No. | Exposure time in hours until CO extinction = 0.3 |
|---|---|
| none | 80 |
| 1 | 2100 |
| 2 | 2420 |
| 3 | 340 |
| 5 | 2325 |

What is claimed is:

1. A compound of the formula I

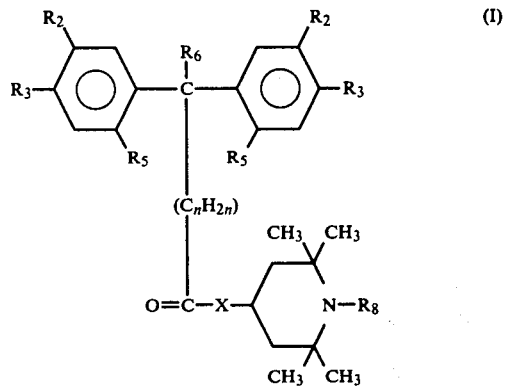

or its acid addition salt, in which $R_2$ is $C_1$–$C_4$-alkyl, $R_3$ is —OH, $R_5$ is hydrogen or methyl, $R_6$ is hydrogen or methyl, $R_8$ is hydrogen, methyl or acetyl, X is —O— or —NH— and n is 0 to 2.

2. The compound according to claim 1, namely 2,2,6,6-tetramethyl-N-acetyl-piperidin-4-yl di-(3-t-butyl-6-methyl-4-hydroxy-phenyl)-acetate.

3. The compound according to claim 1, namely 1,2,2,6,6-pentamethyl-piperidin-4-yl 4,4-di-(4-hydroxy-3-t-butyl-phenyl)-valerate.

4. The compound according to claim 1, namely 4,4-di-(4-hydroxy-3-t-butyl-phenyl)-valeric acid (2,2,6,6-tetramethyl-piperidin-4-yl)-amide.

5. A composition consisting essentially of a plastic and a compound according to claim 1.

* * * * *